US009814263B2

(12) United States Patent
Cochand et al.

(10) Patent No.: US 9,814,263 B2
(45) Date of Patent: Nov. 14, 2017

(54) AEROSOL GENERATING SYSTEM HAVING MEANS FOR DETERMINING DEPLETION OF A LIQUID SUBSTRATE

(75) Inventors: Olivier Cochand, Dombresson (CH); Michel Thorens, Moudon (CH); Jean-Marc Flick, Pomy (CH); Yvan Degoumois, Colombier (CH)

(73) Assignee: Philip Morris Products S.A., Neuchatel (CH)

( * ) Notice: Subject to any disclaimer, the term of this patent is extended or adjusted under 35 U.S.C. 154(b) by 1148 days.

(21) Appl. No.: 13/996,716

(22) PCT Filed: Dec. 22, 2011

(86) PCT No.: PCT/EP2011/073791
§ 371 (c)(1),
(2), (4) Date: Aug. 8, 2013

(87) PCT Pub. No.: WO2012/085203
PCT Pub. Date: Jun. 28, 2012

(65) Prior Publication Data
US 2014/0020693 A1    Jan. 23, 2014

(30) Foreign Application Priority Data
Dec. 24, 2010    (EP) .................................... 10252235

(51) Int. Cl.
*A24F 47/00*    (2006.01)
*A61M 15/06*    (2006.01)
(Continued)

(52) U.S. Cl.
CPC ......... *A24F 47/008* (2013.01); *A61M 11/041* (2013.01); *A61M 11/042* (2014.02);
(Continued)

(58) Field of Classification Search
CPC ......... A24F 47/008; A61M 2205/3389; A61M 2205/3368; A61M 2205/3386;
(Continued)

(56) References Cited

U.S. PATENT DOCUMENTS 2,057,353 A    10/1936    Whittemore, Jr.
4,163,391 A    8/1979    Bezard et al.
(Continued)

FOREIGN PATENT DOCUMENTS

CN    101557728 A    10/2009
CN    101782496 A    7/2010
(Continued)

OTHER PUBLICATIONS

GCE Study Buddy, Heat Capacities, 2014, http://www.gcestudybuddy.com/using-word-documents/heat-capacities, all pages.*

(Continued)

*Primary Examiner* — Michael J Felton
*Assistant Examiner* — Jerzi H Moreno Hernandez
(74) *Attorney, Agent, or Firm* — Oblon, McClelland, Maier & Neustadt, L.L.P.

(57)    ABSTRACT

There is provided an electrically operated aerosol generating system for receiving an aerosol-forming substrate. The system includes a liquid storage portion for storing liquid aerosol-forming substrate, an electric heater including at least one heating element for heating the liquid aerosol-forming substrate, and electric circuitry for determining depletion of liquid aerosol-forming substrate heated by the heater based on a relationship between a temperature of the heating element and power applied to the heating element. There is also provided a method in an electrically operated aerosol generating system including a liquid storage portion for storing liquid aerosol-forming substrate and an electric (Continued)

heater including at least one heating element for heating the liquid aerosol-forming substrate, the method including determining depletion of liquid aerosol-forming substrate heated by the heater based on a relationship between a temperature of the heating element and power applied to the heating element.

17 Claims, 3 Drawing Sheets

(51) Int. Cl.
*A61M 11/04* (2006.01)
*A61M 15/00* (2006.01)
*A61M 16/00* (2006.01)

(52) U.S. Cl.
CPC .......... *A61M 15/008* (2014.02); *A61M 15/06* (2013.01); *A61M 2016/0021* (2013.01); *A61M 2205/3368* (2013.01); *A61M 2205/3386* (2013.01); *A61M 2205/3389* (2013.01); *A61M 2205/3653* (2013.01); *A61M 2205/8206* (2013.01)

(58) Field of Classification Search
CPC .. A61M 2016/0021; A61M 2205/3653; A61M 2205/8206; A61M 11/042; A61M 15/008; A61M 11/041; A61M 15/06
See application file for complete search history.

(56) References Cited

U.S. PATENT DOCUMENTS

| | | | |
|---|---|---|---|
| 4,947,874 A * | 8/1990 | Brooks | A24F 47/008 128/202.21 |
| 5,144,962 A | 9/1992 | Counts et al. | |
| 5,201,223 A | 4/1993 | McQueen | |
| 5,894,841 A | 4/1999 | Voges | |
| 2004/0129793 A1* | 7/2004 | Nguyen | A61M 11/041 239/13 |
| 2008/0257367 A1 | 10/2008 | Paterno et al. | |
| 2009/0126518 A1* | 5/2009 | Meinzinger | A61L 2/208 73/865.9 |
| 2009/0133691 A1* | 5/2009 | Yamada | A61M 11/041 128/200.16 |
| 2009/0272379 A1 | 11/2009 | Thorens et al. | |
| 2009/0283103 A1 | 11/2009 | Nielsen et al. | |
| 2010/0313901 A1* | 12/2010 | Fernando | A24F 47/008 131/330 |
| 2011/0036346 A1* | 2/2011 | Cohen | A61M 15/0065 128/200.14 |
| 2011/0265806 A1* | 11/2011 | Alarcon | A24F 47/00 131/273 |
| 2011/0278189 A1* | 11/2011 | Terry | A24F 47/008 206/459.1 |
| 2012/0048266 A1* | 3/2012 | Alelov | A61M 11/005 128/202.21 |
| 2013/0104916 A1* | 5/2013 | Bellinger | A61M 11/041 131/328 |
| 2013/0186392 A1* | 7/2013 | Haartsen | A61M 15/0065 128/200.23 |
| 2013/0319435 A1* | 12/2013 | Flick | A24F 47/008 131/328 |

FOREIGN PATENT DOCUMENTS

| | | |
|---|---|---|
| DE | 20 2009 010 400 U1 | 12/2009 |
| EP | 0 358 002 A2 | 3/1990 |
| EP | 0 430 559 | 6/1991 |
| EP | 0 532 194 A1 | 3/1993 |
| EP | 2 113 178 A1 | 11/2009 |
| JP | S58-166219 A | 10/1983 |
| JP | 11-89551 A | 4/1989 |
| JP | 3-232481 A | 10/1991 |
| JP | H05-57901 A | 3/1993 |
| JP | H05-220974 A | 8/1993 |
| JP | 6-336024 A | 12/1994 |
| JP | 2000-41654 A | 2/2000 |
| JP | 2004-97617 A | 4/2004 |
| WO | WO 95/01137 A1 | 1/1995 |
| WO | 2007 078273 | 7/2007 |
| WO | WO 2009/118085 A1 | 10/2009 |
| WO | WO 2009/132793 A1 | 11/2009 |

OTHER PUBLICATIONS

University of Missouri. Joule Heating of a Resistor, 2009, http://www.umsl.edu/~physics/files/pdfs/Electricity%20and%20Magnetism%20Lab/Exp6.JouleHeating.pdf, all pages.*
U.S. Appl. No. 13/996,725, filed Jun. 21, 2013, Flick.
International Search Report Issued Apr. 24, 2012 in PCT/EP11/73791 Filed Dec. 22, 2011.
Combined Chinese Office Action and Search Report issued Dec. 31, 2014 in Patent Application No. 201180066556.5 (submitting English language translation only).
Office Action issued Oct. 28, 2015 in Japanese Patent Application No. 2013-545406 (submitting English language translation only).
Office Action issued May 14, 2014 in Colombian Patent Application No. 13-171822-5 (submitting English translation only).
Office Action issued Aug. 3, 2016 in Japanese Patent Application No. 2013-545406 (submitting English language translation only).
Combined Singaporean Office Action and Search Report issued Oct. 14, 2014 in Patent Application No. 2013047741.

* cited by examiner

AEROSOL GENERATING SYSTEM HAVING MEANS FOR DETERMINING DEPLETION OF A LIQUID SUBSTRATE

CROSS REFERENCE TO RELATED APPLICATION

This application is a national phase application based on PCT/EP2011/073791, filed on Dec. 22, 2011.

The present invention relates to an electrically operated aerosol generating system. In particular, the present invention relates to an electrically operated aerosol generating system in which an aerosol-forming substrate is liquid and is contained in a liquid storage portion.

WO 2009/132793 A1 discloses an electrically heated smoking system having a liquid storage portion. The liquid storage portion includes an aerosol-forming substrate and is connected to a vaporizer comprising an electric heater which is powered by a battery supply. In use, the electric heater is activated by suction on a mouthpiece by a user to switch on the battery power supply. The heated aerosol-forming substrate contained in the vaporizer will be vaporized. Suction on a mouthpiece by the user causes air to be drawn along or through the vaporizer thus generating an aerosol which, as known to those skilled in the art, is a suspension of solid particles or liquid droplets in a gas, such as air. The generated aerosol is drawn into the mouthpiece and subsequently into the mouth of a user.

The electrically operated aerosol generating systems of the prior art, including the smoking system referred to above, do have a number of advantages, but there is still opportunity for improvement, particularly concerning the handling of an aerosol-forming substrate contained in a liquid storage portion.

According to a first aspect of the invention, there is provided an electrically operated aerosol generating system for receiving an aerosol-forming substrate, the system comprising: a liquid storage portion for storing liquid aerosol-forming substrate; an electric heater comprising at least one heating element for heating the liquid aerosol-forming substrate; and electric circuitry configured to determine depletion of liquid aerosol-forming substrate based on a relationship between a power applied to the heating element and a resulting temperature change of the heating element.

The electric circuitry is preferably configured to estimate an amount of liquid aerosol-forming substrate in the liquid storage portion based on the determined depletion.

The amount of liquid aerosol-forming substrate in the liquid storage portion may be an absolute amount or a relative amount, e.g. a percentage value, or may be a determination that there is more or less than a threshold amount of liquid aerosol-forming substrate in the liquid storage portion.

Providing electric circuitry for determining depletion of liquid aerosol-forming substrate delivered to the heater is advantageous for a number of reasons. For example, when the liquid storage portion is empty or nearly empty, insufficient liquid aerosol-forming substrate may be supplied to the electric heater. This may mean that the aerosol created does not have the desired properties, for example, aerosol particle size or chemical composition. This may result in a poor experience for the user. In addition, if it can be determined when the liquid storage portion is empty or nearly empty, it may be possible to inform the user. Then the user can prepare to replace or refill the liquid storage portion.

The relationship between a temperature of the heating element and power applied to the heating element may be, for example, a rate of change of temperature of the heating element for a given power applied, an absolute temperature of the heating element at a given time in a heating cycle for a given power applied, an integral of temperature over a portion of a heating cycle for a given power applied or a power applied to the heating element in order to maintain a given temperature. In general terms, the less aerosol-forming substrate is delivered to the heater for vaporisation, the higher the temperature of the heating element will be for a given applied power. For a given power, the evolution of the temperature of the heating element during a heating cycle, and how that evolution changes over a plurality of heating cycles, can be used to detect if there has been a depletion in the amount of aerosol-forming substrate delivered to the heater.

For the liquid aerosol-forming substrate, certain physical properties, for example the vapour pressure or viscosity of the substrate, are chosen in a way to be suitable for use in the aerosol generating system. The liquid preferably comprises a tobacco-containing material comprising volatile tobacco flavour compounds which are released from the liquid upon heating. Alternatively, or in addition, the liquid may comprise a non-tobacco material. The liquid may include water, ethanol, or other solvents, plant extracts, nicotine solutions, and natural or artificial flavours. Preferably, the liquid further comprises an aerosol former. Examples of suitable aerosol formers are glycerine and propylene glycol.

An advantage of providing a liquid storage portion is that the liquid in the liquid storage portion is protected from ambient air. In some embodiments, ambient light cannot enter the liquid storage portion as well, so that the risk of light-induced degradation of the liquid is avoided. Moreover, a high level of hygiene can be maintained.

Preferably, the liquid storage portion is arranged to hold liquid for a predetermined number of puffs. If the liquid storage portion is not refillable and the liquid in the liquid storage portion has been used up, the liquid storage portion has to be replaced by the user. During such replacement, contamination of the user with liquid has to be prevented. Alternatively, the liquid storage portion may be refillable. In that case, the aerosol generating system may be replaced after a certain number of refills of the liquid storage portion.

The electric heater may comprise a single heating element. Alternatively, the electric heater may comprise more than one heating element, for example two, or three, or four, or five, or six or more heating elements. The heating element or heating elements may be arranged appropriately so as to most effectively heat the liquid aerosol-forming substrate.

The at least one electric heating element preferably comprises an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, Constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation. In composite materials, the electrically resistive material may optionally be embedded in, encapsulated or coated with an insulating material or vice-versa, depending on the kinetics of energy transfer and the external physicochemical properties required. The heating element may comprise a metallic etched foil insulated between two layers of an inert material. In that case, the inert material may comprise Kapton®, all-polyimide or mica foil. Kapton® is a registered trade mark of E.I. du Pont de Nemours and Company.

The at least one electric heating element may take any suitable form. For example, the at least one electric heating element may take the form of a heating blade. Alternatively, the at least one electric heating element may take the form of a casing or substrate having different electro-conductive portions, or an electrically resistive metallic tube. The liquid storage portion may incorporate a disposable heating element. Alternatively, one or more heating needles or rods that run through the liquid aerosol-forming substrate may also be suitable. Alternatively, the at least one electric heating element may comprise a flexible sheet of material. Other alternatives include a heating wire or filament, for example a Ni—Cr (Nickel-Chrome), platinum, tungsten or alloy wire, or a heating plate. Optionally, the heating element may be deposited in or on a rigid carrier material.

The at least one electric heating element may comprise a heat sink, or heat reservoir comprising a material capable of absorbing and storing heat and subsequently releasing the heat over time to heat the aerosol-forming substrate. The heat sink may be formed of any suitable material, such as a suitable metal or ceramic material. Preferably, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material such as paper. Other suitable materials which release heat via a reversible phase change include paraffin, sodium acetate, naphthalene, wax, polyethylene oxide, a metal, metal salt, a mixture of eutectic salts or an alloy.

The heat sink or heat reservoir may be arranged such that it is directly in contact with the liquid aerosol-forming substrate and can transfer the stored heat directly to the substrate. Alternatively, the heat stored in the heat sink or heat reservoir may be transferred to the aerosol-forming substrate by means of a heat conductor, such as a metallic tube.

The at least one heating element may heat the liquid aerosol-forming substrate by means of conduction. The heating element may be at least partially in contact with the substrate. Alternatively, the heat from the heating element may be conducted to the substrate by means of a heat conductive element.

Alternatively, the at least one heating element may transfer heat to the incoming ambient air that is drawn through the electrically operated aerosol generating system during use, which in turn heats the aerosol-forming substrate. The ambient air may be heated before passing through the aerosol-forming substrate. Alternatively, the ambient air may be first drawn through the liquid substrate and then heated.

Preferably, the electrically operated aerosol generating system further comprises a capillary wick for conveying the liquid aerosol-forming substrate from the liquid storage portion to the electric heater.

Preferably, the capillary wick is arranged to be in contact with liquid in the liquid storage portion. Preferably, the capillary wick extends into the liquid storage portion. In that case, in use, liquid is transferred from the liquid storage portion to the electric heater by capillary action in the capillary wick. In one embodiment, the capillary wick has a first end and a second end, the first end extending into the liquid storage portion for contact with liquid therein and the electric heater being arranged to heat liquid in the second end. When the heater is activated, the liquid at the second end of the capillary wick is vaporized by the at least one heating element of the heater to form the supersaturated vapour. The supersaturated vapour is mixed with and carried in the air flow. During the flow, the vapour condenses to form the aerosol and the aerosol is carried towards the mouth of a user. The liquid aerosol-forming substrate has physical properties, including viscosity and surface tension, which allow the liquid to be transported through the capillary wick by capillary action.

The capillary wick may have a fibrous or spongy structure. The capillary wick preferably comprises a bundle of capillaries. For example, the capillary wick may comprise a plurality of fibres or threads or other fine bore tubes. The fibres or threads may be generally aligned in the longitudinal direction of the aerosol generating system. Alternatively, the capillary wick may comprise sponge-like or foam-like material formed into a rod shape. The rod shape may extend along the longitudinal direction of the aerosol generating system. The structure of the wick forms a plurality of small bores or tubes, through which the liquid can be transported by capillary action. The capillary wick may comprise any suitable material or combination of materials. Examples of suitable materials are capillary materials, for example a sponge or foam material, ceramic- or graphite-based materials in the form of fibres or sintered powders, foamed metal or plastics material, a fibrous material, for example made of spinned or extruded fibres, such as cellulose acetate, polyester, or bonded polyolefin, polyethylene, terylene or polypropylene fibres, nylon fibres or ceramic. The capillary wick may have any suitable capillarity and porosity so as to be used with different liquid physical properties. The liquid has physical properties, including but not limited to viscosity, surface tension, density, thermal conductivity, boiling point and vapour pressure, which allow the liquid to be transported through the capillary device by capillary action.

Preferably, the at least one heating element is in the form of a heating wire or filament encircling, and optionally supporting, the capillary wick. The capillary properties of the wick, combined with the properties of the liquid, ensure that, during normal use when there is plenty of aerosol-forming substrate, the wick is always wet in the heating area.

The capillary wick and the heater, and optionally the liquid storage portion, may be removable from the aerosol generating system as a single component.

In a first embodiment, the electrically operated aerosol generating system further comprises a temperature sensor for measuring the temperature of the at least one heating element and the electric circuitry is arranged to monitor the temperature of the at least one heating element as sensed by the temperature sensor and determine depletion of liquid aerosol-forming substrate heated by the heater based on the temperature of the at least one heating element as sensed by the temperature sensor.

If the amount of liquid aerosol-forming substrate has decreased, for example if the liquid storage portion is empty or nearly empty, insufficient liquid aerosol-forming substrate may be supplied to the heater. This may result in the temperature of the heating element increasing. Thus, the temperature of the heating element, as sensed by the temperature sensor, may allow the electric circuitry to determine that the amount of liquid aerosol-forming substrate in the liquid storage portion has decreased to a predetermined threshold and may further be able to provide an indication of an absolute amount of liquid aerosol-forming substrate in the liquid storage portion.

In another embodiment, the electric circuitry is arranged to measure the electrical resistance of the at least one heating element, to ascertain the temperature of the heating element from the measured electrical resistance.

If the amount of liquid aerosol-forming substrate has decreased, for example if the liquid storage portion is empty or nearly empty, insufficient liquid aerosol-forming substrate may be supplied to the heater. This may result in the temperature of the heating element increasing. If the at least one heating element has suitable characteristics of the temperature coefficient of resistance, measuring the electrical resistance of the at least one heating element will allow the temperature of the heating element to be ascertained. Thus, the temperature of the heating element, as ascertained by the electric circuitry from the measured electrical resistance, may allow the electric circuitry to determine an amount of liquid aerosol-forming substrate in the liquid storage portion.

An advantage of this embodiment is that it is not necessary to include a temperature sensor, which may take up valuable space in the aerosol generating system and may also be costly. It is emphasized that the electrical resistance, in this embodiment, is used both as an 'actuator' (heating element) and a 'sensor' (temperature measurement).

In this embodiment, the electric circuitry may be arranged to measure the electrical resistance of the at least one heating element by measuring the current through the at least one heating element and the voltage across the at least one heating element and determining the electrical resistance of the at least one heating element from the measured current and voltage. In that case, the electric circuitry may comprise a resistor, having a known resistance, in series with the at least one heating element and the electric circuitry may be arranged to measure the current through the at least one heating element by measuring the voltage across the known-resistance resistor and determining the current through the at least one heating element from the measured voltage and the known resistance.

The electric circuitry may be arranged to determine depletion of liquid aerosol-forming substrate heated by the heater by monitoring an increase of the sensed or ascertained temperature over successive heating cycles as the liquid aerosol-forming substrate in the liquid storage portion is consumed.

The electric circuitry may be arranged to determine depletion of liquid aerosol-forming substrate heated by the heater by monitoring the rate of increase of the sensed or ascertained temperature at the start of a heating cycle, over successive heating cycles as the liquid aerosol-forming substrate in the liquid storage portion is consumed.

The electric circuitry may be arranged to determine an amount of liquid aerosol-forming substrate in the liquid storage portion by monitoring an increase in the value of an integral over time of the sensed or ascertained temperature over a portion of each heating cycle, over successive heating cycles as the liquid aerosol-forming substrate in the liquid storage portion is consumed.

In another embodiment, the electric circuitry is arranged to limit the temperature of the heating element to a maximum temperature, and is arranged to determine depletion of aerosol-forming substrate heated by the heater by monitoring an amount of power applied to the heating element to maintain the maximum temperature.

In this embodiment, the electric circuitry may be arranged to provide power to the heating element in a pulse width modulated signal, and wherein the electric circuitry is arranged to monitor an amount or power applied to the heating element by monitoring the duty cycle of the pulse width modulated signal.

The electric circuitry may be arranged to calibrate other systems for determining an amount of aerosol-forming substrate in the liquid storage portion on the basis of the determined amount.

In addition to allowing for an estimation of an amount of aerosol-forming substrate in the liquid storage portion, the same principle of monitoring the temperature evolution of the heating element during each heating cycle can be used to protect the user from overheating and malfunction if, for example, the viscosity of the liquid aerosol-forming substrate has changed due to extreme external conditions so that it is no longer delivered to the heating element in sufficient quantity.

In a preferred embodiment, the electric circuitry is arranged, when the amount of liquid aerosol-forming substrate in the liquid storage portion is estimated to have decreased to a predetermined threshold, to deactivate the electric heater.

This is advantageous because the user can then no longer use the aerosol generating system once there is insufficient liquid aerosol-forming substrate. This will avoid creation of an aerosol which does not have the desired properties. This will avoid a poor experience for the user.

The electric circuitry may be arranged to deactivate the electric heater by blowing an electrical fuse between the electric heater and an electric power supply. The electric circuitry may be arranged to deactivate the electric heater by switching off a switch between the electric heater and an electric power supply. Alternative methods of deactivating the electric heater will be apparent to the skilled person.

In a preferred embodiment, the electric circuitry is arranged, when the amount of liquid aerosol-forming substrate in the liquid storage portion is estimated to have decreased to the predetermined threshold, to indicate this to a user. This is advantageous because the indication enables the user to refill or replace the liquid storage portion.

The electrically operated aerosol generating system may comprise a user display. In that case, the indication may comprise an indication on the user display. Alternatively, the indication may comprise an audible indication, or any other suitable type of indication for a user.

The aerosol generating system may further comprise an electric power supply. Preferably, the aerosol generating system comprises a housing. Preferably, the housing is elongate. If the aerosol generating includes a capillary wick, the longitudinal axis of the capillary wick and the longitudinal axis of the housing may be substantially parallel. The housing may comprise a shell and a mouthpiece. In that case, all the components may be contained in either the shell or the mouthpiece. In one embodiment, the housing includes a removable insert comprising the liquid storage portion, the capillary wick and the heater. In that embodiment, those parts of the aerosol generating system may be removable from the housing as a single component. This may be useful for refilling or replacing the liquid storage portion, for example.

The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle.

Preferably, the aerosol generating system is portable. The aerosol generating system may be a smoking system and may have a size comparable to a conventional cigar or cigarette. The smoking system may have a total length between approximately 30 mm and approximately 150 mm. The smoking system may have an external diameter between approximately 5 mm and approximately 30 mm.

Preferably, the electrically operated aerosol generating system is an electrically heated smoking system.

According to a second aspect of the invention, there is provided a method comprising: providing an electrically operated aerosol generating system comprising a liquid storage portion for storing liquid aerosol-forming substrate and an electric heater comprising at least one heating element for heating the liquid aerosol-forming substrate; and determining depletion of liquid aerosol-forming substrate heated by the heater based on a relationship between a power applied to the heating element and a resulting temperature change of the heating element.

The amount of liquid aerosol-forming substrate may be an absolute amount or a relative amount, e.g. a percentage value, or may be a determination that there is more or less than a threshold amount of liquid aerosol-forming substrate in the liquid storage portion.

According to a third aspect of the invention, there is provided electric circuitry for an electrically operated aerosol generating system, the electric circuitry being arranged to perform the method of the second aspect of the invention.

According to a fourth aspect of the invention, there is provided a computer program which, when run on programmable electric circuitry for an electrically operated aerosol generating system, causes the programmable electric circuitry to perform the method of the second aspect of the invention.

According to a fifth aspect of the invention, there is provided a computer readable storage medium having stored thereon a computer program according to the fourth aspect of the invention.

Features described in relation to the aerosol generating system of the invention may also be applicable to the method of the invention. And, features described in relation to the method of the invention may also be applicable to the aerosol generating system of the invention.

The invention will be further described, by way of example only, with reference to the accompanying drawings, of which.

Figure 1:
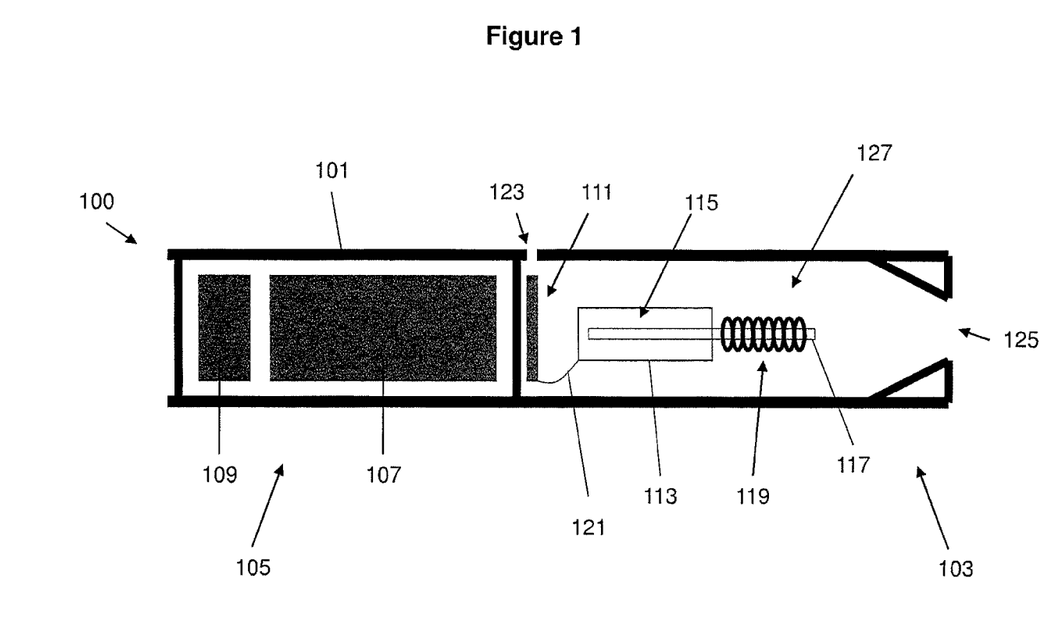
FIG. 1 shows one example of an electrically operated aerosol generating system having a liquid storage portion.

FIG. 1 shows one example of an electrically operated aerosol generating system having a liquid storage portion. In FIG. 1, the system is a smoking system. The smoking system 100 of FIG. 1 comprises a housing 101 having a mouthpiece end 103 and a body end 105. In the body end, there is provided an electric power supply in the form of battery 107 and electric circuitry 109. A puff detection system 111 is also provided in cooperation with the electric circuitry 109. In the mouthpiece end, there is provided a liquid storage portion in the form of cartridge 113 containing liquid 115, a capillary wick 117 and a heater 119. Note that the heater is only shown schematically in FIG. 1. In the exemplary embodiment shown in FIG. 1, one end of capillary wick 117 extends into cartridge 113 and the other end of capillary wick 117 is surrounded by the heater 119. The heater is connected to the electric circuitry via connections 121, which may pass along the outside of cartridge 113 (not shown in FIG. 1). The housing 101 also includes an air inlet 123, an air outlet 125 at the mouthpiece end, and an aerosol-forming chamber 127.

In use, operation is as follows. Liquid 115 is conveyed by capillary action from the cartridge 113 from the end of the wick 117 which extends into the cartridge to the other end of the wick which is surrounded by heater 119. When a user draws on the aerosol generating system at the air outlet 125, ambient air is drawn through air inlet 123. In the arrangement shown in FIG. 1, the puff detection system 111 senses the puff and activates the heater 119. The battery 107 supplies electrical energy to the heater 119 to heat the end of the wick 117 surrounded by the heater. The liquid in that end of the wick 117 is vaporized by the heater 119 to create a supersaturated vapour. At the same time, the liquid being vaporized is replaced by further liquid moving along the wick 117 by capillary action. (This is sometimes referred to as "pumping action".) The supersaturated vapour created is mixed with and carried in the air flow from the air inlet 123. In the aerosol-forming chamber 127, the vapour condenses to form an inhalable aerosol, which is carried towards the outlet 125 and into the mouth of the user.

In the embodiment shown in FIG. 1, the electric circuitry 109 and puff detection system 111 are preferably programmable. The electric circuitry 109 and puff detection system 111 can be used to manage operation of the aerosol generating system. This assists with control of the particle size in the aerosol.

FIG. 1 shows one example of an electrically operated aerosol generating system according to the present invention. Many other examples are possible, however. In addition, note that FIG. 1 is schematic in nature. In particular, the components shown are not to scale either individually or relative to one another. The electrically operated aerosol generating system needs to include or receive a liquid aerosol-forming substrate contained in a liquid storage portion. The electrically operated aerosol generating system requires some sort of electric heater having at least one heating element for heating the liquid aerosol-forming substrate. Finally, the electrically operated aerosol generating system requires electric circuitry for determining an amount of liquid aerosol-forming substrate in the liquid storage portion. This will be described below with reference to FIGS. 2 to 5. For example, the system need not be a smoking system. A puff detection system need not be provided. Instead, the system could operate by manual activation, for example the user operating a switch when a puff is taken. For example, the overall shape and size of the housing could be altered. Moreover, the system may not include a capillary wick. In that case, the system may include another mechanism for delivering liquid for vaporization.

However, in a preferred embodiment, the system does include a capillary wick for conveying the liquid from the liquid storage portion to the at least one heating element. The capillary wick can be made from a variety of porous or capillary materials and preferably has a known, pre-defined capillarity. Examples include ceramic- or graphite-based materials in the form of fibres or sintered powders. Wicks of different porosities can be used to accommodate different liquid physical properties such as density, viscosity, surface tension and vapour pressure. The wick must be suitable so that the required amount of liquid can be delivered to the heater. Preferably, the heater comprises at least one heating wire or filament extending around the capillary wick.

A number of embodiments of the invention will now be described with reference to FIGS. 2 to 5. The embodiments are based on the example shown in FIG. 1, although are applicable to other embodiments of electrically operated aerosol generating systems.

As already mentioned, the aerosol generating system of the invention includes electric circuitry for determining an amount of liquid aerosol-forming substrate in the liquid storage portion. This is advantageous because, when the liquid storage portion is empty or nearly empty, insufficient liquid aerosol-forming substrate may be supplied to the heater. This may mean that the aerosol created and inhaled by the user does not have the desired properties, for example, aerosol particle size. This may result in a poor experience for the user. In addition, it is advantageous to provide a mechanism whereby the user can be informed that the liquid storage portion is empty or nearly empty. Then the user can prepare to replace or refill the liquid storage portion. If a capillary wick is provided, this will mean that the capillary wick will become dry. The temperature of the heating element will increase. This heating element temperature increase is utilised in the first and second embodiments of the invention.

Figure 2:
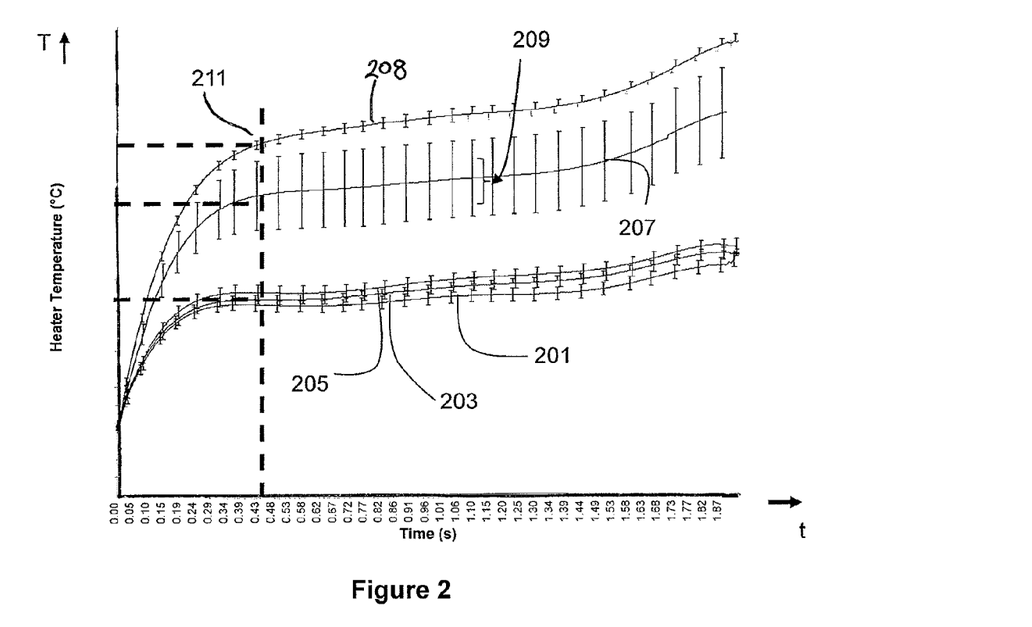
FIG. 2 is a plot showing five medians of temperature profiles of the heating element during multiple puffs of an electrically operated aerosol generating system.

FIG. 2 is a plot showing five medians of temperature profiles being measured during multiple puffs of an aerosol generating system. The temperature, T of the heating element is shown on the y-axis and the puff time t is shown on the x-axis. Curve 201 is the median of a first set of puffs, each puff having a 2-second puff duration. Similarly, curve 203 is the median of a second set of puffs, curve 205 is the median of a third set of puffs, curve 207 is the median of a fourth set of puffs and curve 208 is the median of a fifth set of puffs. In each curve, the vertical bars (for example shown at 209) indicate the standard deviation around the median for those temperatures. Thus, the evolution of the measured temperature over the life of the liquid storage portion is shown. This behaviour was observed and confirmed for all liquid formulations vaporized and for all power levels used.

As can be seen from FIG. 2, the temperature response of the heating element is reasonably stable over curves 201, 203 and 205. That is to say, the standard deviation around the median for the first three sets of puffs is reasonably small. Over curve 207, two effects are noticed. Firstly, the standard deviation around the median for the third set of puffs is greater. Secondly, the temperature of the heating element during each puff has significantly increased. These two effects indicate that the liquid storage portion is becoming empty.

Over curve 208, the standard deviation around the median for the fifth set of puffs is smaller once again. That is to say, the temperature range over the puffs is reasonably stable. However, the temperature of the heating element during each puff has increased further. This indicates that the liquid storage portion is substantially empty.

The temperature increase in curve 207, as compared with curve 205, is particularly evident after around 0.4 seconds of the puff (shown by dotted line 211). Detecting that the amount of liquid in the liquid storage portion has decreased to a threshold can therefore be accurately based on the temperature level of the heating element after 0.4 s of the puff duration.

Empirical data for particular designs of aerosol-forming substrate and for the particular system design can be stored in memory in the electric circuitry. This empirical data can relate the temperature of the heating element at a particular point in a puff or heating cycle operating at a given power with the amount of liquid remaining in the liquid storage portion. The empirical data can then be used to determine how much liquid is remaining and may be used to provide a user with an indication when there is estimated to be less than a predetermined number of puffs remaining.

Thus, FIG. 2 demonstrates that there is a clear temperature increase of the heating element as the liquid storage portion becomes empty. This is particularly evident after the first 0.4 seconds of a puff. This temperature increase can be utilized to determine when the liquid storage portion is empty or nearly empty.

It can also be seen in FIG. 2 that the slope of the temperature profile between 0 seconds and 0.2 seconds increases as the liquid storage portion becomes empty. Thus, a measure of the rate of temperature increase during an initial time of a puff over the life of the liquid storage portion can provide an alternative or additional means to detect an amount of the remaining liquid in the liquid storage portion. This measure may indeed be a more desirable measure than that of FIG. 2, because the measure may be taken over a shorter period of time i.e. 0.2 seconds rather than 2 seconds. This may provide a faster insight into the temperature level change and may assist in reducing the risk of poor aerosol properties.

Figure 3:
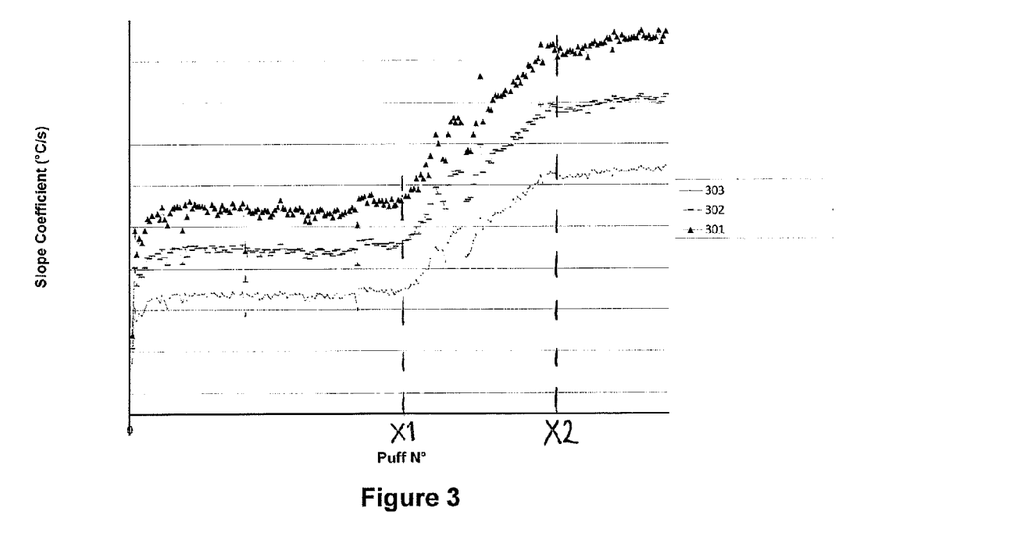
FIG. 3 is a plot showing the rate of temperature increase of the heating element over the entire life of a liquid storage portion, calculated at three different time periods.

FIG. 3 is a plot showing the temperature rate of increase calculated for different time ranges during the consumption of the aerosol-forming substrate in the liquid storage portion, using a constant power. The plotted points were calculated using the formula:

$$a = \frac{\Delta T}{\Delta t} = \frac{T_1 - T_0}{t_1 - t_0}.$$

Plot 301 shows the rate of temperature increase or slope coefficient with $t_1=2$ ms and $t_2=50$ ms from the onset of each puff, plot 302 shows the slope coefficient with $t_1=20$ ms and $t_2=100$ ms from the onset of each puff, and plot 303 shows slope coefficient with $t_1=20$ ms and $t_2=200$ ms from the onset of each puff. It can be seen that the slope coefficient during a puff is quite constant from puff number zero, when the liquid storage portion is full to about puff number 'X1', for all three plots. Between puff number 'X1' and puff number 'X2' there is an increase in the slope coefficient as the puff number increases. It can be seen that this increase in the slope coefficient is approximately linear with puff number for all three plots. The increase in rate of temperature rise for a given applied power is a result of depletion of aerosol-forming substrate in the vicinity of the heater as a result of emptying of the liquid storage portion. In this example, this leads to drying of the wick. From puff number X2 onwards the slope coefficient is again fairly constant. This corresponds to an empty liquid storage portion and a dry wick. There is no aerosol-forming substrate to vaporize and so the energy supplied to the heating element is all directed simply to heating. This behavior was observed and confirmed for all liquid formulations used and for all power levels.

The linear behavior of the rate of temperature increase in the "emptying" region between X1 and X2 puffs can be exploited to provide a measure of the amount of aerosol-forming substrate remaining in the liquid storage portion. It can also be used to calibrate any other techniques used for measuring or estimating the remaining aerosol-forming substrate. It can be seen from FIG. 3 that curve 301, corresponding to the rate of temperature increase between 2 and 50 ms from the onset of each puff, provides the greatest change between puffs X1 and X2 and so can be used to provide the greatest resolution of the amount of aerosol-forming substrate remaining in the liquid storage portion. This also allows a calculation of remaining aerosol-forming substrate to be made very quickly following the onset of each puff.

It should be clear that the onset of the emptying region and the rate of temperature rise in the emptying region is dependent on the composition of the aerosol forming substrate and the physical properties of the system, such as the system dimensions. So using a different device design or a different substrate will alter the behavior of the device in the emptying region. A threshold for deciding that the storage portion is "empty" can be set as appropriate to the system design and substrate being used.

An alternative to the measurement of slope shown in FIG. 3 is to integrate under the curves in FIG. 2. This may be done over the same time range of between 0 seconds and 0.2 seconds of each puff. This could also be a more desirable measure than that of FIG. 2, because the measure would be taken over only 0.2 seconds and hence could provide a faster insight into the temperature level change.

Thus, FIGS. 2 and 3 show that a measure of the heating element temperature, or rate of change of temperature, or an integral of temperature over time, can all provide a sufficiently accurate measure of when the amount of liquid storage portion has decreased to a threshold.

According to the first embodiment of the invention, the amount of liquid in the liquid storage portion is determined by measuring the temperature close to the heating element. As discussed above, if the measured temperature increases from puff to puff, this may indicate that the liquid storage portion is empty or nearly empty.

According to the first embodiment of the invention, a temperature sensor is provided in the aerosol generating system close to the heating element. The electric circuitry can monitor the temperature measured by the temperature sensor and hence determine an amount of liquid in the liquid storage portion. The advantage of this embodiment is that no calculation or derivation is required, since the temperature sensor directly measures the temperature close to the heating element.

Once it has been determined when the amount of liquid in the liquid storage portion has decreased to a threshold, a number of actions may be taken and these will be described below.

According to the second embodiment of the invention, the amount of liquid in the liquid storage portion is determined by measuring the resistance of the electric heating element. If the heating element has suitable temperature coefficient of resistance characteristics, (for example, see equation (5) below), then the resistance may provide a measure of the temperature of the electric heating element.

Figure 4:
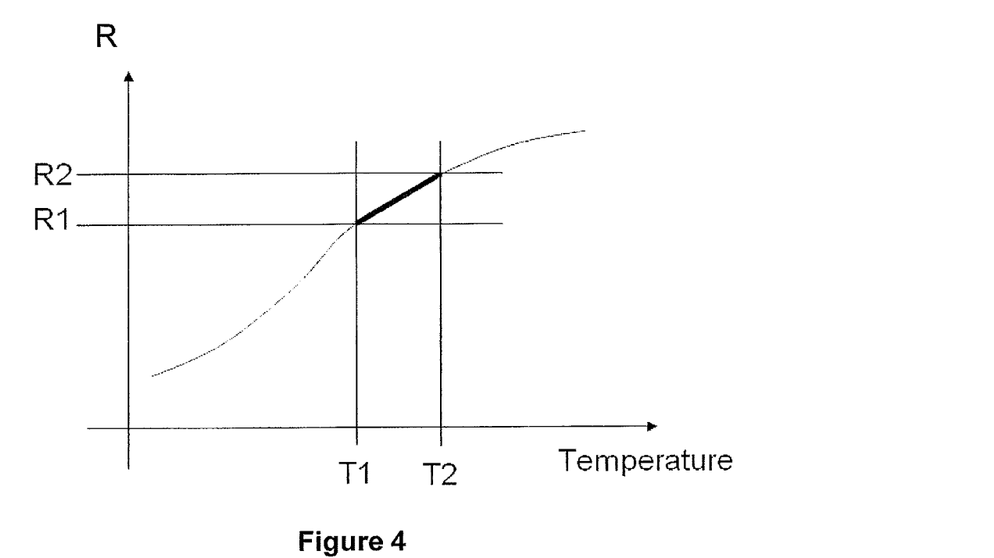
FIG. 4 is a plot showing, on the y-axis, heating element resistance and, on the x-axis, heating element temperature of an electric heater of an electrically operated aerosol generating system.

FIG. 4 is a plot showing the resistance, R of the heating element of the electric heater on the y-axis, versus the temperature, T of the heating element on the x-axis. As can be seen in FIG. 4, as the temperature T of the heating element increases, so does the resistance R. Within a selected range (between temperatures T1 and T2 and resistances R1 and R2 in FIG. 4), the temperature T and resistance R may be proportional to one another.

As discussed above in relation to the first embodiment of the invention, if the liquid storage portion is empty or nearly empty, insufficient liquid aerosol-forming substrate will be supplied to the heater. This will mean that any capillary wick will become dry, and the temperature of the heating element will increase. FIG. 4 shows that such a temperature increase may be determined by a measure of the resistance of the heating element because, as the temperature increases, so will the measured resistance.

Figure 5:
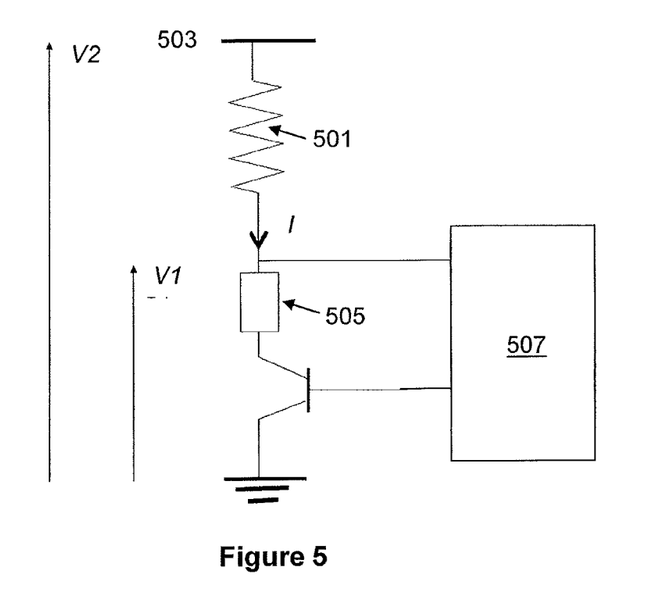
FIG. 5 is a schematic circuit diagram, which allows heating element resistance to be measured, according to one embodiment of the invention.

FIG. 5 is a schematic electric circuit diagram showing how the heating element resistance may be measured according to the second embodiment of the invention. In FIG. 5, the heater 501 is connected to a battery 503 which provides a voltage V2. The heater resistance to be measured at a particular temperature is $R_{heater}$. In series with the heater 501, an additional resistor 505, with known resistance r is inserted connected to voltage V1, intermediate between ground and voltage V2. In order for microprocessor 507 to measure the resistance $R_{heater}$ of the heater 501, the current through the heater 501 and the voltage across the heater 501 can both be determined. Then, the following well-known formula can be used to determine the resistance:

$$V = IR \qquad (1)$$

In FIG. 5, the voltage across the heater is V2−V1 and the current through the heater is I. Thus:

$$R_{heater} = \frac{V2 - V1}{I} \qquad (2)$$

The additional resistor 505, whose resistance r is known, is used to determine the current I, again using (1) above. The current through the resistor 505 is I and the voltage across the resistor 505 is V1. Thus:

$$I = \frac{V1}{r} \qquad (3)$$

So, combining (2) and (3) gives:

$$R_{heater} = \frac{(V2 - V1)}{V1} r \qquad (4)$$

Thus, the microprocessor 507 can measure V2 and V1, as the aerosol generating system is being used and, knowing the value of r, can determine the heater's resistance at a particular temperature, $R_{heater}$. By monitoring $R_{heater}$ over the life of the liquid storage portion, an increase in $R_{heater}$ can be determined. Hence, an increase in resistance, which may indicate a temperature increase because the capillary wick is dry, can be detected.

Then, the following formula can be used to determine the temperature T from the measured resistance $R_{heater}$ at temperature T:

$$T = \frac{R_{heater}}{\alpha R_0} + T_0 - \frac{1}{\alpha} \qquad (5)$$

where α is the thermal resistivity coefficient of the heating element material and $R_0$ is the resistance of the heating element at room temperature $T_0$. Thus, an increase in temperature, which may correspond to the liquid storage portion being empty or nearly empty, can be detected.

An advantage of this embodiment is that no temperature sensor, which can be bulky and expensive, is required.

Thus, a measure of the temperature of the heating element can be derived. This can be used to determine when the amount of liquid in the liquid storage portion has decreased to a threshold and to estimate an absolute amount of aerosol-forming substrate remaining in the liquid storage portion.

In a third embodiment of the invention, the aerosol generating system may be configured to maintain or control the temperature of the heating element during a puff, or may be configured to limit the temperature of the heating element to a maximum temperature to avoid unwanted chemical degradation. In this embodiment, instead of using temperature as an indicator of depleting liquid levels, the power required to maintain a predetermined temperature may be used to calculate an amount of aerosol-forming substrate in the liquid storage portion. For example, if a capillary wick is used, as the wick dries less power will be required to maintain a predetermined temperature.

Power may be provided to the heater as a pulse width modulated (PWM) waveform having predetermined amplitude. The duty cycle of the power waveform, i.e. the ratio of the period of time power is on to the period of time when power is off, may then be used a parameter to calculate an amount of aerosol-forming substrate in the liquid storage portion. Again, empirical data relating power to the amount of aerosol-forming substrate in the liquid storage portion may be stored in a memory within the electric circuitry.

In all the embodiments described above, once it has been determined when the amount of liquid aerosol-forming substrate in the liquid storage portion has decreased to a threshold, one or more actions may be taken. The electric heater may be deactivated. For example, a system may be triggered to render the liquid storage portion unusable. For example, the electric circuitry, on determining that the amount of liquid aerosol-forming substrate in the liquid storage portion, has decreased to a threshold, may blow an electrical fuse between the at least one heating element of the electric heater and an electric power supply. The electrical fuse may be provided as part of a removable component including the liquid storage portion. Alternatively, the electric circuitry, on determining that the amount of liquid aerosol-forming substrate in the liquid storage portion, has decreased to a threshold, may switch off a switch between the at least one heating element of the electric heater and an electric power supply. Alternative methods of deactivating the electric heater are, of course, possible. An advantage of deactivating the electric heater is that it is then impossible to use the aerosol generating system. This renders it impossible for a user to inhale an aerosol which does not have the desired properties.

Once it has been determined when the amount of liquid in the liquid storage portion has decreased to a threshold, the user may be advised. For example, the electric circuitry, on determining that the amount of liquid aerosol-forming substrate in the liquid storage portion, has decreased to a threshold, may indicate this to a user. For example, if the aerosol generating system includes a user display, it may be indicated to the user, via the user display, that the liquid storage portion is empty or nearly empty and may provide an estimate of the number of remaining puffs. Alternatively or additionally, an audible sound may indicate to the user that the liquid storage portion is empty or nearly empty. Alternative methods of indicating to the user that the liquid storage portion is empty or nearly empty are, of course, possible. An advantage of advising the user is that the user is then able to prepare to replace or refill the liquid storage portion.

Thus, according to the invention, the electrically operated aerosol generating system includes electric circuitry for determining when the amount of liquid aerosol-forming substrate in the liquid storage portion has decreased to a predetermined threshold. Various methods of determining that the amount of liquid aerosol-forming substrate in the liquid storage portion has decreased to a predetermined threshold have been described with reference to FIGS. 2 to 5. Features described in relation to one embodiment may also be applicable to another embodiment.

The invention claimed is:

1. An electrically operated aerosol generating system for receiving a liquid aerosol-forming substrate, the system comprising:
   a liquid storage portion configured to store the liquid aerosol-forming substrate;
   an electric heater comprising at least one heating element configured to heat the liquid aerosol-forming substrate; and
   electric circuitry including a processor programmed to determine a depletion of the liquid aerosol-forming substrate delivered proximate to the electric heater based on a temperature change of the at least one heating element identified by the processor, data corresponding to power, from a power supply via an electrical connection of the electrically operated aerosol generating system, applied to the at least one heating element, and a change in a relationship between the power applied to the at least one heating element and the identified temperature change of the at least one heating element.

2. The electrically operated aerosol generating system according to claim 1, wherein the processor of the electric circuitry is programmed to estimate an amount of liquid aerosol-forming substrate in the liquid storage portion based on the determined depletion.

3. The electrically operated aerosol generating system according to claim 1, further comprising a temperature sensor configured to measure a temperature of the at least one heating element, and wherein the processor of the electric circuitry is programmed to monitor the temperature of the at least one heating element as sensed by the temperature sensor and determine depletion of liquid aerosol-forming substrate heated by the electric heater based on the temperature as sensed by the temperature sensor.

4. The electrically operated aerosol generating system according to claim 1, wherein the processor of the electric circuitry is programmed to apply a predetermined power from the power supply to the at least one heating element.

5. The electrically operated aerosol generating system according to claim 1, wherein the processor of the electric circuitry is programmed to measure the electrical resistance of the at least one heating element, to ascertain the temperature of the at least one heating element from the measured electrical resistance.

6. The electrically operated aerosol generating system according to claim 5, wherein the processor of the electric circuitry is programmed to measure the electrical resistance of the at least one heating element by measuring current through the at least one heating element and voltage across the at least one heating element, and to determine the electrical resistance of the at least one heating element from the measured current and voltage.

7. The electrically operated aerosol generating system according to claim 3, wherein the processor of the electric circuitry is programmed to determine depletion of liquid aerosol-forming substrate heated by the electric heater by monitoring an increase of the sensed temperature over successive heating cycles as the liquid aerosol-forming substrate in the liquid storage portion is consumed.

8. The electrically operated aerosol generating system according to claim 5, wherein the processor of the electric circuitry is programmed to determine depletion of liquid aerosol-forming substrate heated by the electric heater by monitoring an increase of the ascertained temperature over successive heating cycles as the liquid aerosol-forming substrate in the liquid storage portion is consumed.

9. The electrically operated aerosol generating system according to claim 3, wherein the processor of the electric circuitry is programmed to determine depletion of liquid aerosol-forming substrate heated by the electric heater by monitoring the rate of increase of the sensed temperature over a portion of each heating cycle, over successive heating cycles as the liquid aerosol-forming substrate in the liquid storage portion is consumed.

10. The electrically operated aerosol generating system according to claim 5, wherein the processor of the electric circuitry is programmed to determine depletion of liquid aerosol-forming substrate heated by the electric heater by monitoring the rate of increase of the ascertained temperature over a portion of each heating cycle, over successive heating cycles as the liquid aerosol-forming substrate in the liquid storage portion is consumed.

11. The electrically operated aerosol generating system according to claim 3, wherein the processor of the electric circuitry is programmed to determine depletion of liquid aerosol-forming substrate heated by the electric heater by monitoring an increase in the value of an integral over time of the sensed temperature over a portion of each heating cycle, over successive heating cycles as the liquid aerosol-forming substrate in the liquid storage portion is consumed.

12. The electrically operated aerosol generating system according to claim 5, wherein the processor of the electric circuitry is programmed to determine depletion of liquid aerosol-forming substrate heated by the electric heater by monitoring an increase in the value of an integral over time of the ascertained temperature over a portion of each heating cycle, over successive heating cycles as the liquid aerosol-forming substrate in the liquid storage portion is consumed.

13. The electrically operated aerosol generating system according to claim 1, wherein the processor of the electric circuitry is programmed to limit the temperature of the at least one heating element to a maximum temperature, and to determine depletion of aerosol-forming substrate heated by the electric heater by monitoring an amount of power applied to the at least one heating element to maintain the maximum temperature.

14. The electrically operated aerosol generating system according to claim 1, further comprising a capillary wick configured to convey the liquid aerosol-forming substrate from the liquid storage portion to the electric heater.

15. Electric circuitry for an electrically operated aerosol generating system for receiving a liquid aerosol-forming substrate, the system comprising a liquid storage portion configured to store the liquid aerosol-forming substrate, an electric heater including at least one heating element configured to heat the liquid aerosol-forming substrate, and the electric circuitry,
wherein the electric circuitry includes a processor programmed to determine a depletion of the liquid aerosol-forming substrate delivered proximate to the electric heater and heated by the electric heater based on a temperature change of the at least one heating element identified by the processor, data corresponding to power, from a power supply via an electrical connection of the electric circuitry, applied to the at least one heating element, and a change in a relationship between the power applied to the at least one heating element and the identified temperature change of the at least one heating element.

16. A method, comprising:
providing an electrically operated aerosol generating system comprising a liquid storage portion configured to store a liquid aerosol-forming substrate, and an electric heater comprising at least one heating element configured to heat the liquid aerosol-forming substrate; and
determining, using a processor, a depletion of the liquid aerosol-forming substrate delivered proximate to the electric heater and heated by the electric heater based on a temperature change of the at least one heating element identified by the processor, data corresponding to power applied to the at least one heating element, and a change in a relationship between the power applied to the at least one heating element and the identified temperature change of the at least one heating element.

17. A nontransitory computer readable storage medium encoded with a computer program product, which when run on programmable electric circuitry for an electrically operated aerosol generating system for receiving a liquid aerosol-forming substrate, the system comprising a liquid storage portion configured to store the liquid aerosol-forming substrate, an electric heater including at least one heating element configured to heat the liquid aerosol-forming substrate and electric circuitry, causes the programmable electric circuitry to perform the steps of the method of claim 16.

* * * * *